United States Patent
Reinhardt et al.

(10) Patent No.: US 10,517,752 B2
(45) Date of Patent: Dec. 31, 2019

(54) ORTHOSIS WITH AT LEAST ONE TEXTILE BANDAGE

(75) Inventors: Holger Reinhardt, Kempen (DE); Helle Hormes, Northeim (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 13/805,979

(22) PCT Filed: May 25, 2011

(86) PCT No.: PCT/DE2011/001106
§ 371 (c)(1),
(2), (4) Date: Dec. 20, 2012

(87) PCT Pub. No.: WO2012/006984
PCT Pub. Date: Jan. 19, 2012

(65) Prior Publication Data
US 2013/0092179 A1  Apr. 18, 2013

(30) Foreign Application Priority Data
Jul. 1, 2010 (DE) .......................... 10 2010 026 240

(51) Int. Cl.
*A61F 5/00* (2006.01)
*A61F 5/37* (2006.01)

(52) U.S. Cl.
CPC .................................. *A61F 5/3738* (2013.01)

(58) Field of Classification Search
CPC ........ A61F 5/3723; A61F 5/37; A61F 5/3738; A61F 5/0118; A61F 5/013; A61F 5/373

USPC ................................ 602/20, 4; 128/878, 864
See application file for complete search history.

(56) References Cited

U.S. PATENT DOCUMENTS

| | | |
|---|---|---|
| 3,008,466 A | 11/1961 | Adam |
| 3,404,680 A | 10/1968 | Gutman et al. |
| 5,397,296 A | 3/1995 | Sydor et al. |

(Continued)

FOREIGN PATENT DOCUMENTS

| | | |
|---|---|---|
| CN | 2242596 Y | 12/1996 |
| CN | 101242792 A | 8/2008 |

(Continued)

OTHER PUBLICATIONS

PCT International Search Report for International Application No. PCT/DE2011/001106, dated Dec. 21, 2011.

*Primary Examiner* — Victoria J Hicks
(74) *Attorney, Agent, or Firm* — Holland & Hart, LLP

(57) ABSTRACT

An orthosis with at least one holding element for placing on a body part and securing the holding element with at least one securing member, with which two ends of the holding element bearing on the body part can be connected to each other with tensioning. The at least one holding element is designed without a stable shaped part and allows the bandage to be applied using one hand because the holding element has at least one elastic expansion part, which does not perform the function of a shaped part adapted to the body part and which pretensions the holding element in such a starting shape that the ends of the holding element jut out from the body part, and, with the securing member, the ends of the holding element can be applied to the body part counter to the pretensioning of the expansion part.

10 Claims, 7 Drawing Sheets

(56) References Cited

U.S. PATENT DOCUMENTS

| | | | |
|---|---|---|---|
| 5,403,268 A * | 4/1995 | Clement | A61F 5/3738 |
| | | | 128/DIG. 19 |
| 5,713,837 A | 2/1998 | Grim et al. | |
| 2008/0039757 A1 | 2/2008 | Nordt, III et al. | |
| 2010/0210985 A1 * | 8/2010 | Kuorak | A61F 5/3723 |
| | | | 602/20 |

FOREIGN PATENT DOCUMENTS

| | | |
|---|---|---|
| DE | 3242592 A1 | 5/1984 |
| DE | 3511250 A1 | 11/1985 |
| WO | 2009017442 A1 | 2/2009 |

* cited by examiner

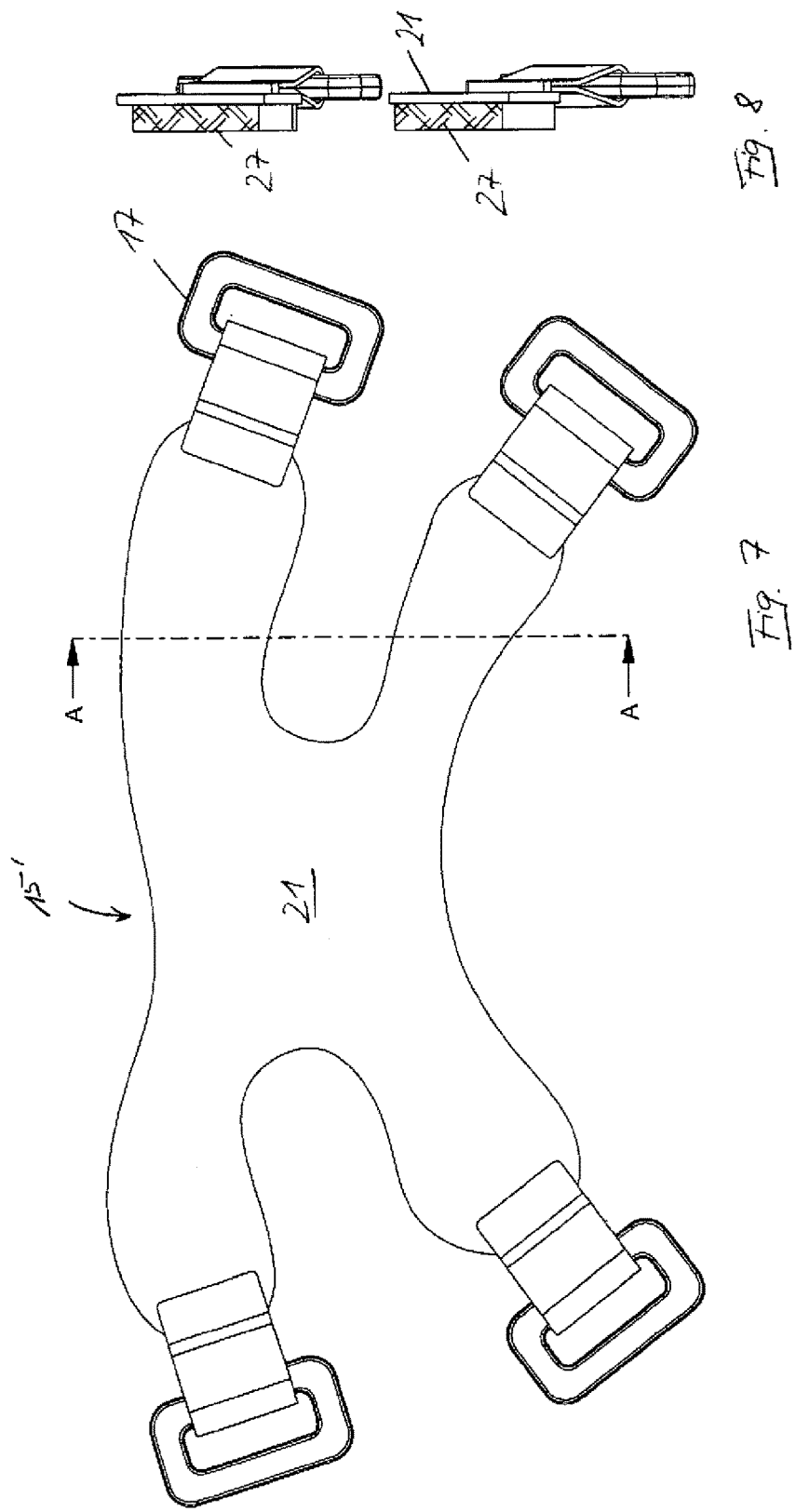

ORTHOSIS WITH AT LEAST ONE TEXTILE BANDAGE

The invention relates to an orthosis with at least one holding element for placing on a body part and securing the holding element with at least one securing means, by which two ends of the holding element bearing on the body part can be connected to each other with tensioning, the at least one holding element being designed without a stable shaped part.

Orthoses of this kind are produced and used in numerous configurations. In particular, orthoses with textile bandages as holding elements have proven useful in stroke patients who are paralyzed on one side after the stroke. For these patients, it is important that the shoulder, arm and hand on the paralyzed side of the body are fixed in order not to be exposed to the risk of injuries caused by uncontrolled movements.

A known orthosis system for hemiparesis patients is composed of a shoulder part, a support part for the elbow joint and, if appropriate, a wrist orthosis. The shoulder part is looped with securing bands around the upper body and guided under the armpit on the healthy side of the body. The shoulder part engages over a part of the upper arm and is connected by a securing strip to the elbow part. The known orthosis is effective and cost-efficient, since it is made from inexpensive textile bandages. The textile bandage engaging over the shoulder is designed by suitable darts in such a way that it can adapt in shape to the shape of the shoulder and engage over the upper arm. However, the use of textile bandages has the disadvantage that these constitute a slack starting material that has to be applied to the body parts in order then to be secured with the flexible securing means, which are generally composed of textile bands provided with velcro fasteners. A helper is therefore needed to fit the orthosis in place, and therefore the patient becomes mobile only when a helper is available to fit the orthosis.

There is therefore a need for orthosis systems to be able to put on using one hand, for example in order to allow hemiparesis patients themselves to fit the orthosis required for the paralyzed half of the body and thus recover a considerable degree of independence.

There are of course other cases where it would be advantageous to fit an orthosis using one hand. The corresponding orthosis can also be a leg orthosis, ankle orthosis or similar.

It is known that orthoses to be fitted using one hand can be designed with shaped parts that are adapted to the body parts onto which the orthosis is fitted. However, orthoses of this kind are expensive to produce, since they generally have to be tailor-made for the particular patient. In addition, the shaped parts are not as comfortable to use as textile bandages, which can be worn inconspicuously under clothing.

It is therefore the object of the present invention to design an orthosis which can be fitted and secured using one hand, is inexpensive to produce and is inconspicuous when being worn.

In order to achieve this object, according to the invention, an orthosis of the type mentioned at the outset is characterized in that the holding element has at least one elastic expansion part, which does not perform the function of a shaped part adapted to the body part and which pretensions the holding element in such a starting shape that the ends of the holding element jut out from the body part, and, with the securing means, the ends of the holding element can be applied to the body part counter to the pretensioning of the expansion part.

The orthosis according to the invention thus uses holding elements which are not pre-shaped and can be textile bandages of the kind that have proven useful in many applications. The supporting function of the orthosis is therefore exerted by the respective slack holding element, without a stable shaped part adapted to the circumferential shape of the body part. According to the invention, the holding element is provided with at least one elastic expansion part, by which the holding element is pretensioned in a starting shape in which the ends of the holding element jut out from the body part. It is thus possible to apply the holding element to the body part using one hand and grip the preferably flexible securing means with which the holding element is fixed to the body part, by virtue of the fact that the ends of the holding element are applied to the body part counter to the pretensioning of the expansion part.

The expansion part according to the invention, preferably applied to that side of a textile bandage facing away from the body, thus has the effect that the textile bandage which is itself slack is brought into a starting shape in which the textile bandage is in itself sorted and can also be prepared for tensioning with the securing means, as will be explained in more detail below. The starting shape of the textile bandage can therefore in particular be tunnel-shaped, such that the bandage in the starting shape can be fitted, for example, over the shoulder, or the elbow joint or the forearm can be placed into the bandage. The starting shape results from the corresponding preparation of the textile bandage, not from the elastic expansion part which simply ensures the required pretensioning but is not designed as a shaped part adapted to the body part.

A suitable shape of the expansion part can be achieved simply by the fact that the textile bandage at suitable points, preferably near the edge of the bandage, is tensioned by the expansion part in the starting shape.

The expansion part does not have the function of a shaped part adapted to the body part and can therefore be designed with a very weak pretensioning force. The pretensioning force must simply be sufficient to tension the textile bandage in the starting shape. No supporting function for the body part has to be obtained thereby. Accordingly, the textile bandage can also be applied easily, and without great force, to the body part counter to the pretensioning of the expansion part.

In an alternative embodiment, particularly for very simple orthoses, the expansion part can also be used without a textile bandage if it is provided with at least one padded section for resting on the body part in question. The expansion part is not a shaped part adapted to the circumferential shape of the body part and does not have the dimensional stability of a shaped part, and instead it merely serves to ensure a substantially flat starting shape from which the expansion part is drawn toward the body part by the securing means, so as to bear on the body part.

In conjunction with the holding element, the securing means will generally loop round the respective body part in order to fix the holding element on the body part, such that the supporting or holding function desired of the orthosis is achieved.

The securing means is preferably a textile securing band that can provide the securing function together with velcro fastener elements. The securing band can be made from an elastic or preferably non-elastic textile material.

In order to fix the holding element, the securing band can expediently be connected to at least two points of the holding element. However, it is also possible to connect a securing band only on one side to the holding element and to provide the securing band for looping round the body part with the holding element, in which case the securing band is fixed onto itself, for example by means of a velcro fastener.

In one embodiment that is preferred because it permits easier handling, the securing band, at one of the securing points to the holding element, is guided through an eyelet and turned back through 180°. Advantageously, the turned-back portion can be held with a widened area captively in the eyelet. This results in advantageous fixing of the securing band for the unfitted orthosis, which is present in the expanded form through the expansion part. The securing band can determine the starting shape of the holding element, which is expanded by the elastic expansion part, and can close the holding element, for example, on the open side of a tunnel-shaped starting shape. The corresponding holding element can be fitted on an arm, for example, by means of the hand and the forearm being inserted into the tunnel and by means of the holding band, with its tunnel-shaped channel, being pulled over the paralyzed hand and forearm, for example in order to be positioned on the elbow joint. By tightening of the securing bands, the fixing on the body part, for example on the elbow joint, can then take place by means of the securing band being fixed on itself by the velcro fastener or on a suitable location of the holding element.

The invention is explained in more detail below on the basis of illustrative embodiments depicted in the drawing, in which:

FIG. 7 shows a view of a holding element of an elbow orthosis in an alternative embodiment to FIG. 4;

FIG. 8 shows a section through the holding element according to FIG. 7.

Figure 1:
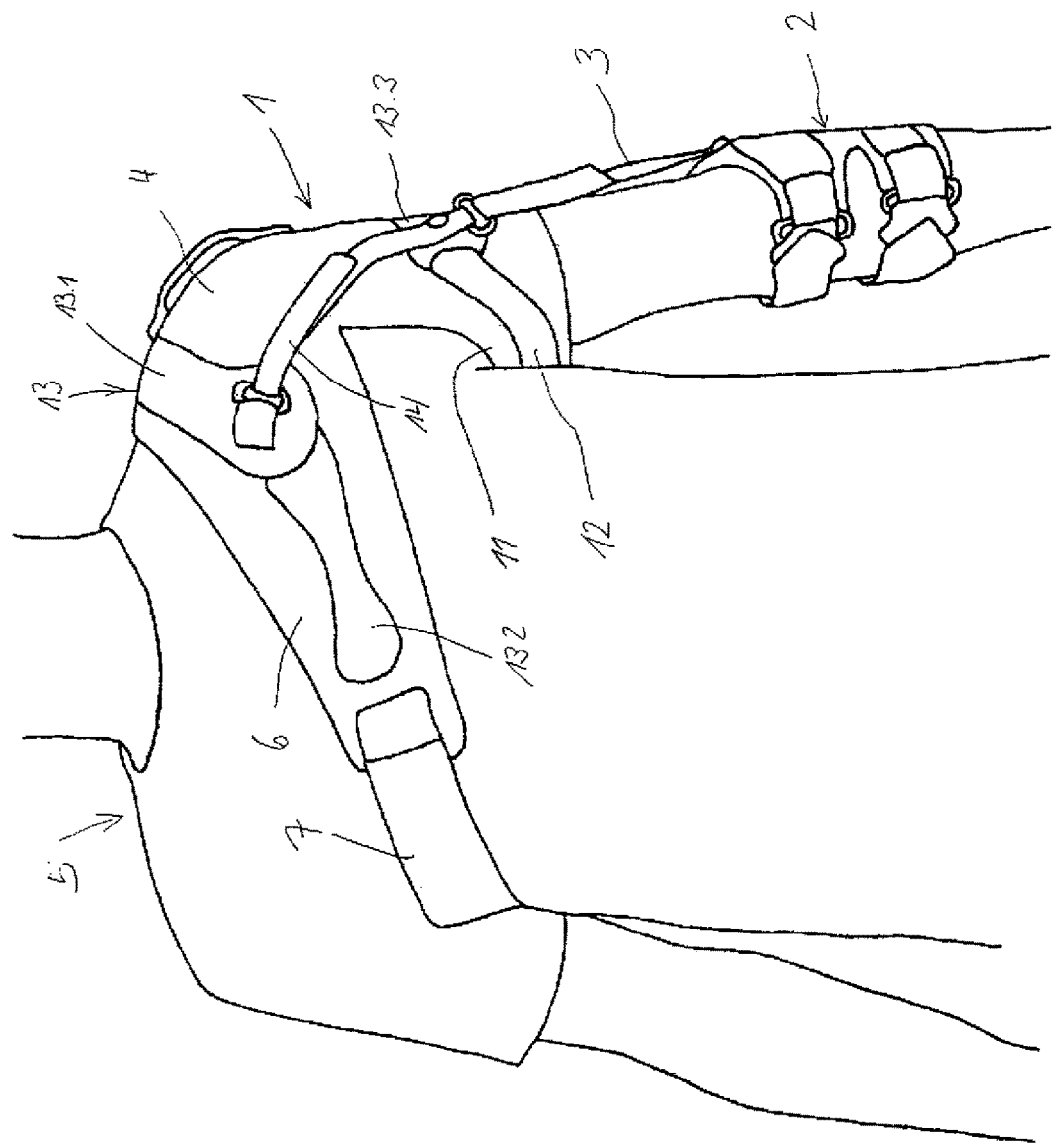
FIG. 1 shows a partial front view of a patient wearing a hemiparesis orthosis.
Figure 2:
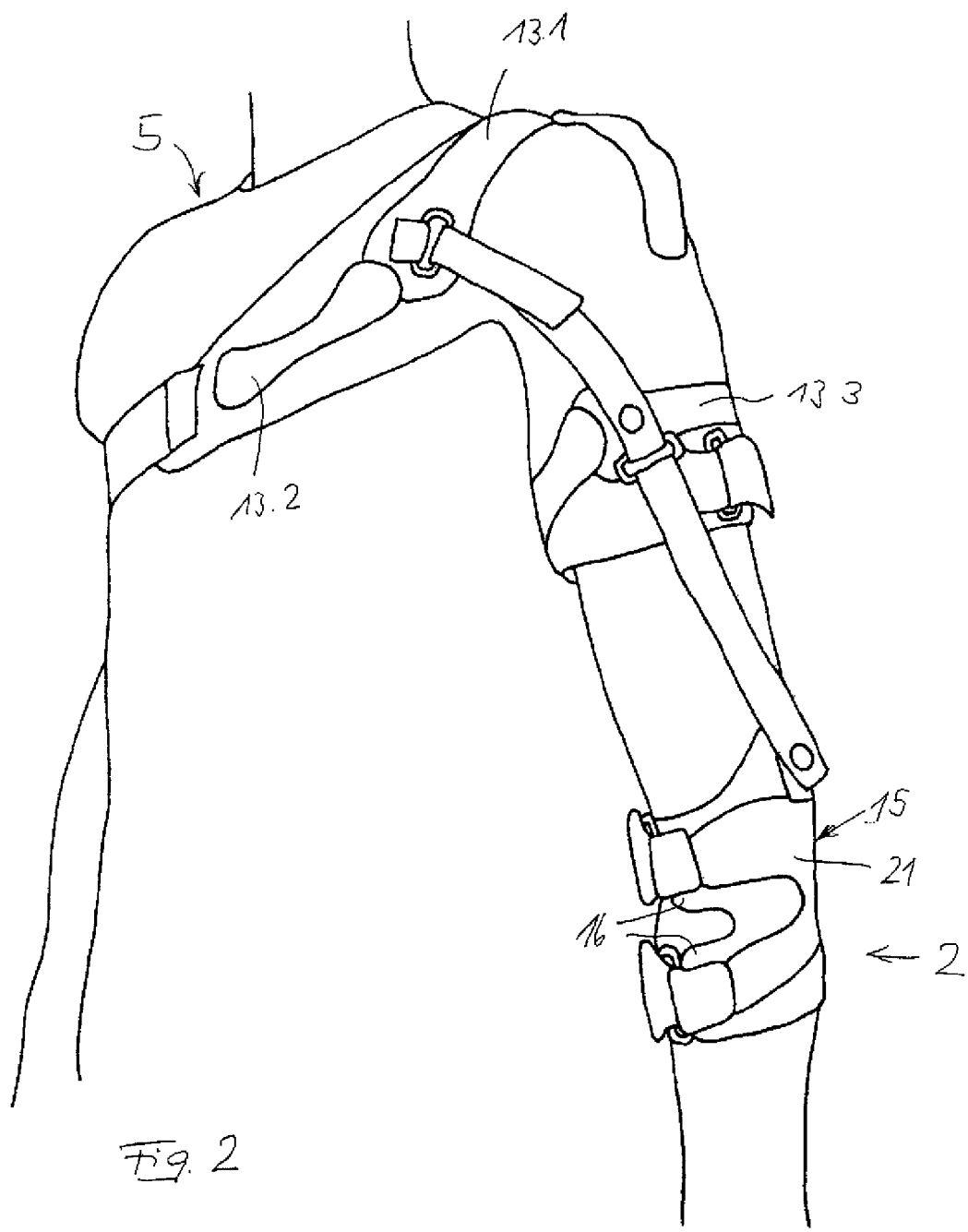
FIG. 2 shows the view in FIG. 1 obliquely from in front.
Figure 3:
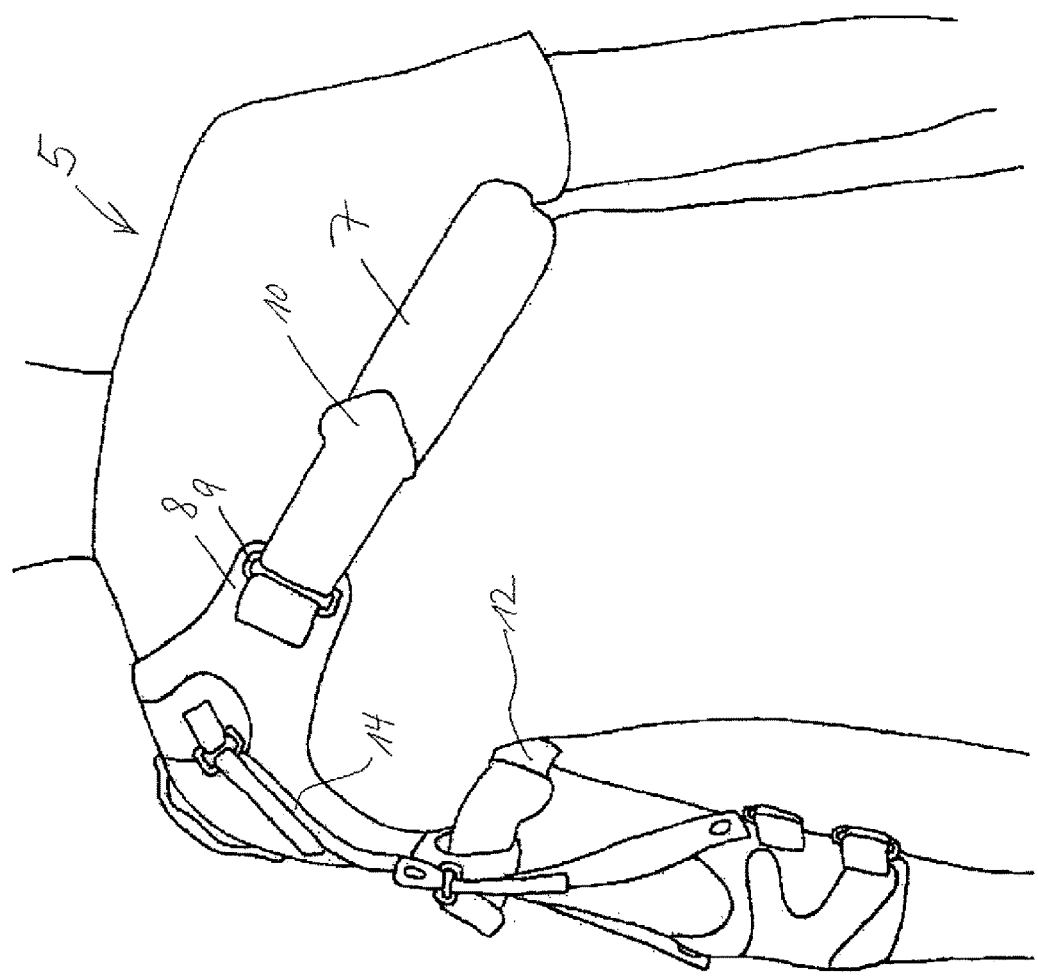
FIG. 3 shows the view in FIG. 1 from the rear.

The hemiparesis orthosis shown in FIGS. 1 to 3 is composed of a shoulder joint part 1 and an elbow part 2, which are connected to each other by a connecting band 3.

The shoulder joint part 1 is composed of a textile bandage as holding element 4 which, from above, extends over the shoulder joint, the ball of the shoulder, and the upper arm of a patient 5. A larger arm 6 narrowing conically across the front of the patient extends over the upper chest area of the patient 5. At its end is secured a securing band 7, which serves as a flexible securing means. As FIGS. 1 and 3 illustrate, the securing band 7 extends around the body of the patient 5 and is guided under the armpit on the healthy side of the patient. On the patient's back (FIG. 3), the securing band 7 extends obliquely upward to an arm 8 of the textile bandage 4. There, the securing band is guided through an eyelet 9 and is fixed on itself via a triangular, arrow-shaped widened end 10. For this purpose, the relevant faces of the securing band 7 and the arrow-shaped end 10 are provided with corresponding parts of a velcro fastener.

The textile bandage 4 extends onward with another arm under the armpit on the paralyzed side of the patient 5 and is likewise provided there with a securing band 12 as a flexible securing means. The securing band 12 extends around the upper arm on the inner aspect thereof and, after looping round the upper arm starting from the back of the patient 5, lies on the textile bandage 4 and is fixed there, for example once again with a velcro fastener.

On the face directed away from the body of the patient 5, the textile bandage is provided with several expansion parts 13, which can be sewn onto the textile bandage. The expansion parts 13 may be referred to as elastic expansion members or at least one elastic expansion member. A first expansion part 13.1 extends from the front to the back of the patient 5 over the upper face of the shoulder. On the back of the patient 5, the expansion part 13.1 ends in the area of the arm 8 present there, as is shown in FIG. 3. On the front, the expansion part 13.1 is adjoined by a further strip-shaped expansion part 13.2, which extends into the area of the arm 6 of the textile bandage and ends near the point where the securing band 7 is secured on this arm 6.

A further expansion part 13.3 is provided in the upper arm area and extends perpendicularly with respect to the longitudinal extent of the humerus of the patient 5. It will be seen that the securing band 12 is secured in the area of the expansion part 13.3. Extending between the expansion parts 13.1 and 13.3, there are also adjusting bands 14 with which the curvature of the textile bandage 4 can be adapted to some extent to the patient 5.

The expansion parts 13 are composed of flat, thin and elastic plastic strips, which are cut out from a flat plastic material. Insofar as they are deformed by the shape of the textile bandage 4, they have a tendency to return to the flat starting position and as such are biased toward a flat position. Thus, the expansion parts 13 pretension the textile bandage 4 when the expansion parts 13 are deformed by the textile bandage 4. In this way, the arms 6, 8 and 11 stand more or less rectilinearly from the rest of the textile bandage 4 when the orthosis is removed from the body of the patient 5 and no tension is exerted between the arms 6, 8 or on the arm 11 via the securing bands 7, 12, respectively. The central portion of the textile bandage 4, from which the arms 6, 8 and 11 issue, is adapted more or less to the shape of the shoulder and the upper arm by darts, this involving only an approximate adaptation to the typical shape of a shoulder joint and upper arm. The textile bandage 4 is fixed on the body of the patient 5 via the arms 6, 8, 11 and with the securing bands 11, 12, which respectively extend round the upper body and the upper arm of the patient 5.

Figure 4:
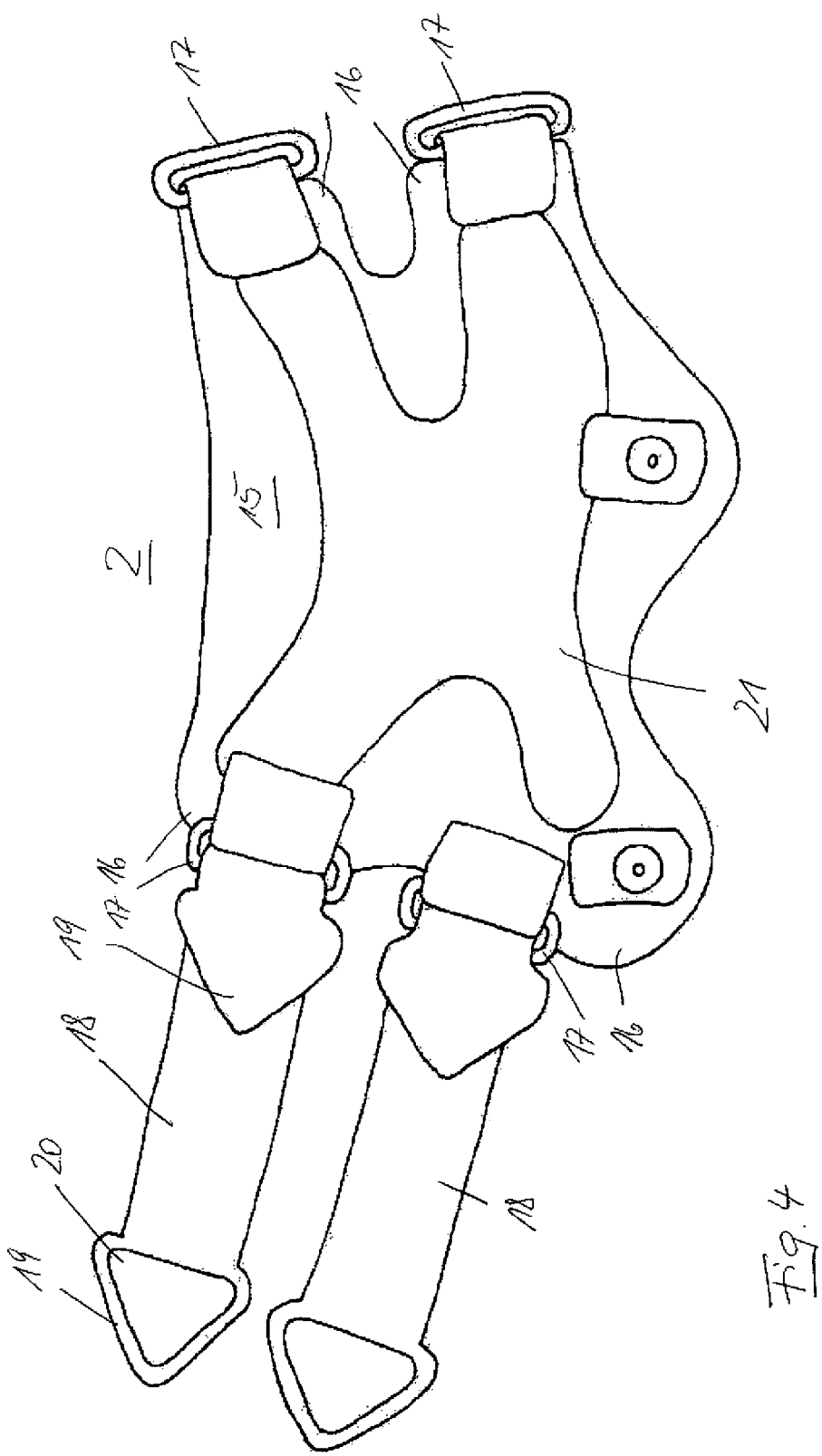
FIG. 4 shows a view of an elbow orthosis as a separate part.

The elbow part is likewise composed of a flat textile bandage as holding element 15, which is formed by a substantially square textile section with four arms 16, as is illustrated in particular in FIG. 4. An eyelet 17 is secured on each of the four arms 16. Two securing bands 18 as flexible securing means are, as non-elastic bands, finished at both ends of their length with arrow-shaped widened ends 19. The arrow-shaped ends 19 are provided on their inner face with a triangular velcro fastener 20, which forms a mating velcro fastener for the inner surface of the securing band 18. For example, the inner surface of the securing bands can be designed with a loop material, while the velcro fastener parts 20 have an associated hook material. The inner surface of the securing bands 18 is the surface onto which the arrow-shaped ends 19 can be turned back for the purpose of fixing them. The inner surface of the securing bands 18 is therefore located on the same side of the securing bands 18 as the velcro fastener parts 20, as is illustrated in FIG. 4.

In the view in FIG. 4, the securing bands 18 are pulled with only one of their arrow-shaped ends through an eyelet 17. In this way, the securing bands 18 do not apply any tension to the arms 16 of the textile bandage 15. The latter is thus pretensioned by an expansion part 21 in a flat starting shape. When the free arrow-shaped ends 19 of the securing bands 18 in FIG. 4 are inserted through the free eyelets 17 in FIG. 4, tension is applied to the textile bandage 15 by the length of the securing bands 18. This bandage 15 is thus bent into a U-shape counter to the pretensioning of the expansion part 21. The respective arms 16 are then connected to each other by a rectilinearly tensioned securing band 18. The arms 16 form ends of the textile bandage 15 of which the opening angle through the securing bands 18 is much greater than the width of the arm of the patient 5 in the area of the elbow. Thus, the textile bandage 15 curved in a U-shape forms, with the securing bands 18, an insert channel into which the hand and the drooping arm of the patient 5 on the paralyzed side can be comfortably inserted, with the bandage 15 being pulled on over the hand and the forearm of the patient 5.

To put on the orthosis according to FIGS. 1 to 3, the elbow part 2 is therefore brought into the described fitting position and hangs down from the shoulder joint part 1. By pulling the elbow part on over the hand and forearm of the patient 5, the elbow part reaches the position on the elbow of the patient 5. In this position, the shoulder joint part can be placed over the shoulder and upper arm of the patient 5. On account of the expansion parts 13, a loop can be formed by the securing band 7 together with the textile bandage 4, and the healthy arm can be placed through this loop, such that the securing band 7, in the securing position shown in FIGS. 1 to 3, can extend under the armpit of the healthy arm of the patient 5 and round the upper body. By then tightening the securing band 12 for looping round the upper arm, the shoulder joint part 8 is fixed in the position of use. The two securing bands 18 of the elbow part are then tightened and finally positioned on the elbow.

Figure 5:
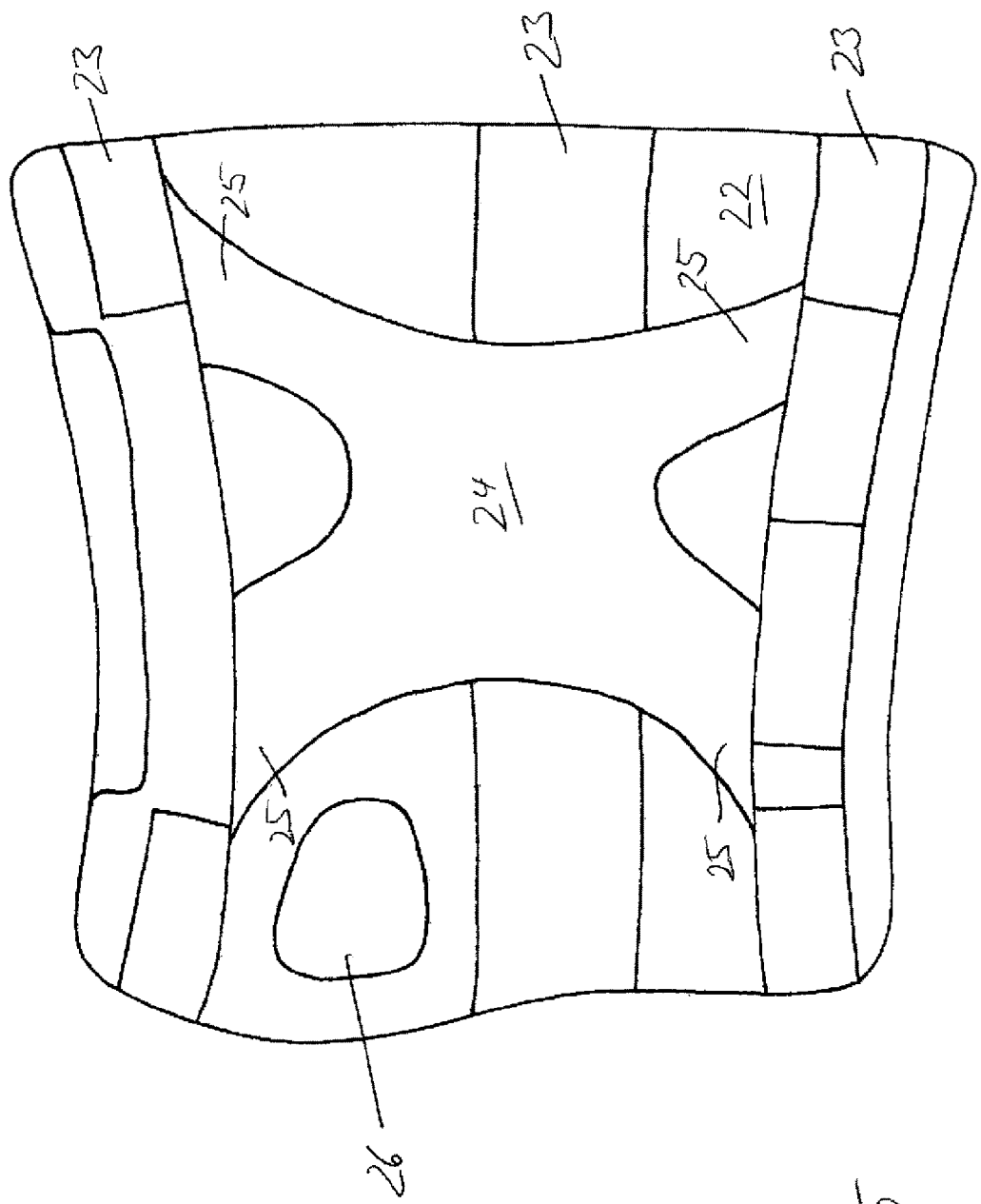
FIG. 5 shows a view of a wrist orthosis as a separate part.
Figure 6:
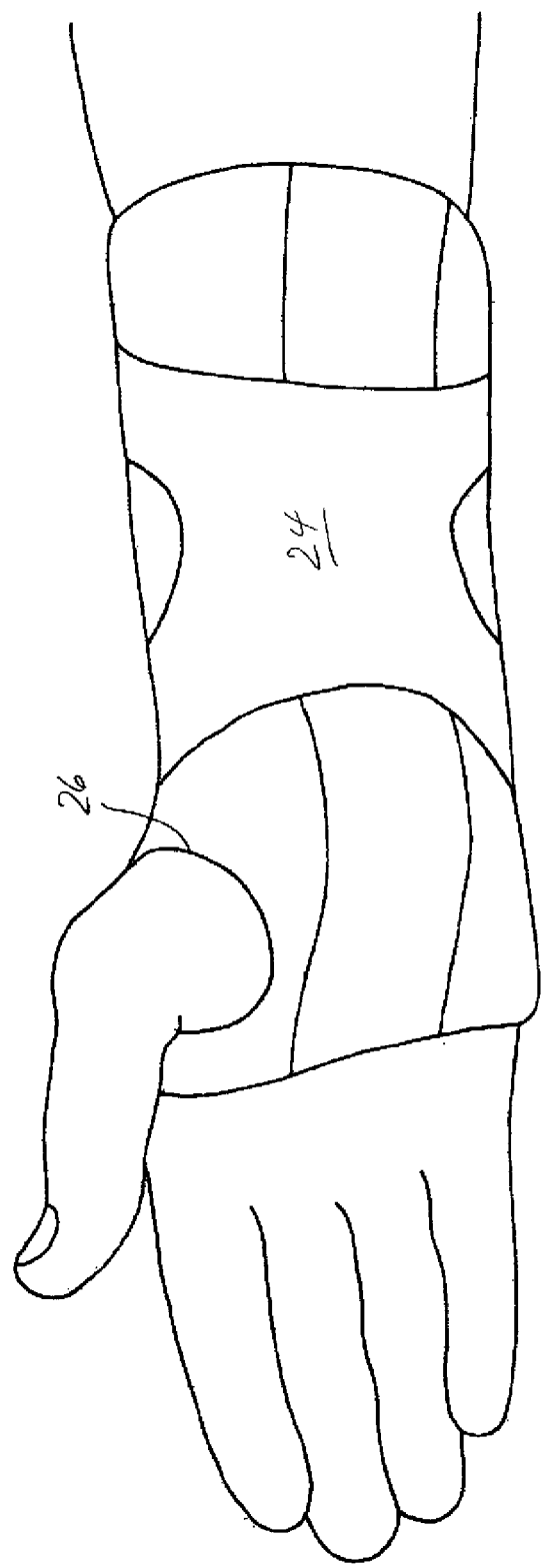
FIG. 6 shows a view of the wrist orthosis from FIG. 5 fitted on the arm of a patient.

In addition, a wrist orthosis can then also be fitted, which is shown in the starting state in FIG. 5 and in the fitted state in FIG. 6.

According to FIG. 5, the wrist orthosis is composed of a substantially rectangular textile bandage as holding element 22, which is strengthened by three textile longitudinal strips 23 sewn onto it.

A substantially X-shaped expansion part 24 extends with four arms 25 up to two strengthening strips 23 on the longitudinal edge of the bandage 22. A through-opening 26 allows a thumb of the paralyzed hand of the patient 5 to be passed through, as is illustrated in FIG. 6.

FIG. 6 does not show the closure of the wrist orthosis with securing strips or the like. This closure is possible in the same way as in the elbow part 2 according to FIG. 4.

FIG. 6 shows that the wrist orthosis is fitted such that the expansion part 24 comes to lie substantially on the inner aspect of the wrist. However, this is not necessarily the case. The wrist orthosis can also be easily fitted from the outside inward and with one hand.

FIG. 7 shows a the elbow orthosis according to 4, in which the holding element 15' is formed by the expansion part 21 itself. The eyelets 17 are thus secured directly on the expansion part 21.

FIG. 8 shows that the expansion part 21 is provided with padded sections 27 on its face directed toward the body part, such that the expansion part 21 can lie comfortably on the body part. As a comparison with FIG. 4 shows, the shape of the expansion part 21 corresponds to the shape of the expansion part 21 on the textile bandage 15 in FIG. 4. Since the textile bandage 15 in FIG. 4 simply has the task of forming the connection to the eyelets 17, the modification in FIG. 7 lies only in securing the eyelets 17 directly to the arms of the expansion part 21. The elbow orthosis according to FIGS. 7 and 8 is fitted in exactly the same way as the elbow orthosis according to FIG. 4.

The illustrative embodiments show that, with the expansion parts 13, 21 and 24 according to the invention, the orthosis can be fitted by one hand, even with more complicated forms of textile bandages 4, 15 and 22, such that the patient 5 can fit the orthosis in place himself and does not rely on assistance from a helper. In the context of the present invention, the holding element 4, 5, 22 can be provided with a dimensionally stable reinforcement, but the latter is not adapted in the circumferential direction to the shape of the body part. For example, in a wrist orthosis, a splint extending in the longitudinal direction of the arm and of the hand can be integrated in the expansion part 21 or in the textile bandage 15.

Of course, the principle of the orthoses set out in the examples can also be applied to ankle orthoses, leg orthoses or also trunk orthoses. In all cases, it is particularly advantageous if the securing bands 7, 12, 18 are held permanently in the eyelets 9, 17 in the manner shown and thereby also cause a pre-shaping of the textile bandage.

The invention claimed is:

1. An orthosis, comprising:
   at least one holding element for placing on a body part;
   at least one securing band operable to secure the at least one holding element to the body part;
   wherein two ends of the at least one holding element are configured to bear on the body part and can be connected to each other with tensioning, the at least one holding element being designed without a stable shaped part;
   at least one elastic expansion member provided as a distinct piece from and secured to the at least one holding element and extending along the at least one holding element in a direction in which the at least one holding element is configured to wrap around the body part, the at least one elastic expansion member pretensioning the at least one holding element when the at least one elastic expansion member is deformed by the at least one holding element, the pretension being configured to cause ends of the at least one holding element to jut out from the body part to form a tunnel shaped starting shape that is open on one side, the at least one elastic expansion member and the at least one holding element being configured to circumferentially wrap around the body part and close the open side of the tunnel shaped starting shape when the at least one holding element is secured to the body part by the at least one securing band, the at least one elastic expansion member being biased toward a flat position;
   wherein the orthosis is adapted to be fitted and secured to the body part with one hand using the at least one securing band, the ends of the at least one holding element are configured to be applied with the at least one securing band to the body part counter to the pretensioning of the at least one elastic expansion member.

2. The orthosis as claimed in claim 1, wherein the at least one securing band can be connected to at least two points of the at least one holding element.

3. The orthosis as claimed in claim 2, wherein the at least one securing band is configured to be guided at one of the at least two points through an eyelet and turned back through 180°.

4. The orthosis as claimed in claim 3, wherein a turned-back portion of the at least one securing band is held with a widened area captively in the eyelet.

5. The orthosis as claimed in claim 1, wherein the at least one holding element is a textile bandage.

6. The orthosis as claimed in claim 5, wherein the textile bandage, in an expanded starting shape, is pre-shaped to adapt to the body part on which the textile bandage is intended to be placed.

7. The orthosis as claimed in claim 1, wherein the at least one holding element lies flat in an expanded starting shape.

8. The orthosis as claimed in claim 1, wherein the at least one elastic expansion member includes at least one padded section configured to be directed toward the body part.

9. The orthosis as claimed in claim 1, wherein the at least one elastic expansion member extends near an edge of the at least one holding element.

10. An orthosis, comprising:
- at least one holding element for placing on a body part, the at least one holding element having ends configured to wrap around the body part;
- at least one elastic expansion member provided as a distinct piece from and secured to a portion of the at least one holding element and extending in a direction in which the at least one holding element is configured to wrap around the body part, the at least one elastic expansion member being configured to pretension the at least one holding element when the at least one elastic expansion member is deformed by the at least one holding element, the pretensioning biasing the at least one holding element toward an undeformed position of the at least one elastic expansion member, the pretensioning being configured to cause the ends to jut out from the body part to form a tunnel shaped starting shape that is open on one side to facilitate securing of the orthosis to the body part with one hand, the at least one elastic expansion member being biased toward a flat position;
- at least one securing band configured to secure the at least one holding element to the body part against the pretensioning and close the open side of the tunnel shaped starting shape.

* * * * *